US006492551B1

United States Patent
Paatero et al.

(10) Patent No.: US 6,492,551 B1
(45) Date of Patent: Dec. 10, 2002

(54) METHOD FOR MANUFACTURING ALKALI METAL OR ALKALINE-EARTH METAL FORMATE

(75) Inventors: Erkki Paatero, Kauniainen (FI); Marko Lahtinen, Helsinki (FI); Kari Saari, Vantaa (FI); Pekka Vapaaoksa, Tampere (FI)

(73) Assignee: Kemira Chemicals OY, Helsinki (FI)

( * ) Notice: Subject to any disclaimer, the term of this patent is extended or adjusted under 35 U.S.C. 154(b) by 0 days.

(21) Appl. No.: 09/787,080

(22) PCT Filed: Sep. 24, 1999

(86) PCT No.: PCT/FI99/00789

§ 371 (c)(1),
(2), (4) Date: Apr. 16, 2001

(87) PCT Pub. No.: WO00/18717

PCT Pub. Date: Apr. 6, 2000

(30) Foreign Application Priority Data

Sep. 25, 1998 (FI) .................................. 982076

(51) Int. Cl.[7] .......................... C07C 53/02; C07C 53/04; C07C 53/06
(52) U.S. Cl. ...................................... 562/609
(58) Field of Search ........................ 562/609

(56) References Cited

U.S. PATENT DOCUMENTS

| 2,913,318 A | 11/1959 | Erasmus et al. |
| 4,327,070 A | 4/1982 | Meyers |
| 4,479,877 A | 10/1984 | Guter |

FOREIGN PATENT DOCUMENTS

| DE | 41 26 730 | | 2/1993 |
| GB | 1033030 | | 7/1963 |
| GB | 1033030 | * | 6/1966 |
| WO | WO96/01250 | | 1/1996 |

OTHER PUBLICATIONS

"Equilibrium and Column Behavior of Exchange Resins. Strong Base Anion Exchange Resin" R. Kunin and F. X. McGarvey. Industrial and Engineering Chemistry. vol. 41, No. 6 pp1265–1268. (1949).*
Ion Exchangers in Analytical Chemistry by Olof Samuelson. Published by John Wiley and Sons (.*

* cited by examiner

Primary Examiner—Richard L. Raymond
Assistant Examiner—Zachary C. Tucker
(74) Attorney, Agent, or Firm—Swidler Berlin Shereff Friedman, LLP

(57) ABSTRACT

A method for manufacturing alkali metal or alkaline-earth metal formate, starting from a formate anion comprises at least the following sequential steps: A) conversion of a solid anion exchanger to formate form by feeding into it a solution containing a formate anion, B) exchanging the formate anion in the anion exchanger for a replacing anion by feeding into it an alkali metal or alkaline-earth metal salt solution of this replacing anion, C) recovering the alkali metal or alkaline-earth metal formate solution eluted from the anion exchanger during the exchange of the formate anion. The anion exchanger is converted to formate form by feeding into it a sodium formate solution, a formic acid solution or a solution which contains both sodium formate and formic acid. The method can be used for production of potassium formate or calcium formate.

12 Claims, 7 Drawing Sheets

METHOD FOR MANUFACTURING ALKALI METAL OR ALKALINE-EARTH METAL FORMATE

Figure 1:
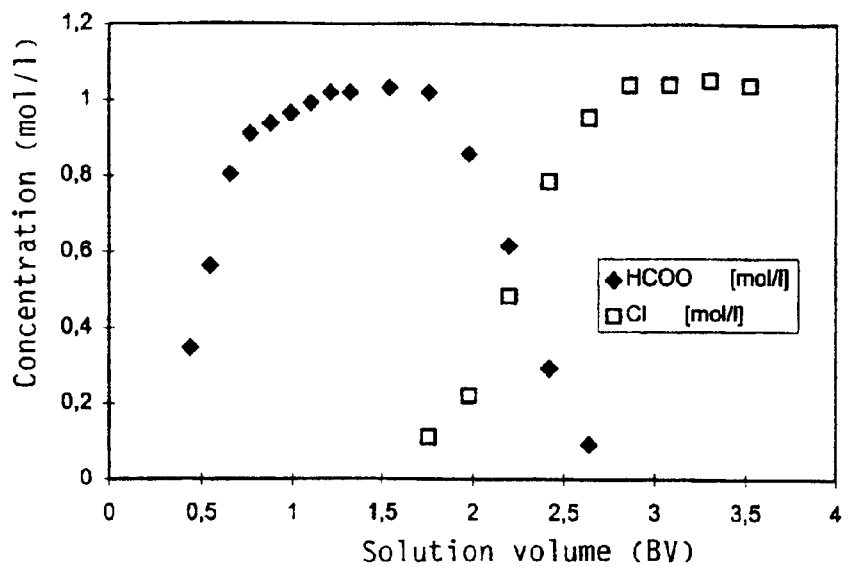

The invention relates to a method for manufacturing alkali metal or alkaline-earth metal formate, starting from a formate anion.

At the present, for example potassium formate is normally manufactured as a neutralization reaction between formic acid and potassium hydroxide, wherein formic acid must always be available. Also a direct synthesis between CO and KOH is a possible manufacturing technique for obtaining potassium formate directly (Encyclopedia of Chemical Technology, 3rd ed., vol. 18, p. 938). This latter reaction requires the application of a high temperature and pressure.

It is characteristic in all these methods that the raw material is potassium hydroxide, and when potassium formate is manufactured in a neutralization reaction, formic acid must always be used as a source of formate anion.

Sodium formate is obtained as a side product of pentaerythritol. Pentaerythritol is manufactured in a reaction between formaldehyde and acetaldehyde by using sodium hydroxide as a catalyst. A side product of this process is dilute sodium formate which can be further converted to formic acid with sulphuric acid.

In connection with this process, also electrodialytic manufacture of potassium formate from $K_2SO_4$ and HCOONa has been developed. An electrodialytic process with a concentrated sodium formate solution and a potassium sulphate solution as starting materials is described in international publication WO 96/01250. The electrodialytic manufacturing process starting from said materials requires various types of selective membranes. Furthermore, the electrodialytic device also requires much maintenance for securing its faultless operation, e.g. to prevent clogging of the membranes.

Swiss patent 439249, to which corresponds British patent 1033030, discloses a method for manufacturing inorganic and organic salts. Table 1 and example 5 of the patent present the conversion of formic acid into sodium formate with a weak-base anion exchanger in liquid form by mixing an aqueous solution of formic acid and sodium chloride with the weak-base anion exchanger dissolved in an organic phase. The manufacturing method requires the dissolving of the anion exchanger in a suitable organic solvent which is insoluble in water, mixing of the substances and separating the water phase for separating the final product.

Methods for manufacturing potassium formate, in turn, are disclosed in U.S. Pat. No. 2,913,318 and DE application publication 4126730. The methods are based on reactions between calcium hydroxide and carbon monoxide and between calcium hydroxide and formaldehyde, respectively. The former method requires a pressure reactor, and the latter requires handling of formaldehyde.

It is an aim of the invention to eliminate the above-mentioned draw-backs and to present a simpler manufacturing method which is suitable for industrial use and in which it is possible to start from a suitable formate solution or formic acid, ie. in principle from any substance containing the formate anion, and to obtain an alkali metal or alkaline-earth metal formate as a final product.

A simple way of manufacturing potassium formate was surprisingly found when studying anion exchange with solid ion exchangers between potassium chloride and sodium formate, wherein the ion exchange produced a potassium formate solution from a sodium formate solution or even from formic acid. In a corresponding way, a possibility was found to produce a calcium formate solution from a sodium formate solution or from formic acid.

Anion exchange processes have been primarily used to purify substances, and examples that can be mentioned include for example the removal of nitrate from drinking water, which is described in U.S. Pat. No. 4,479,877. It is also known to use a weakly basic anion exchanger to remove formic acid in the manufacture of pure formalin (J. T. McNulty, "The many faces of ion-exchange resins", Chemical Engineering, June 1997, p. 99). The manufacture of alkali metal formate or alkaline-earth metal formate by anion exchange with a solid anion exchanger has not been previously disclosed.

In the following, the invention will be described in more detail with reference to the appended drawings which illustrate the steps of the anion exchange process under different conditions.

According to the invention, a solution containing formate ions is supplied to a solid anion exchange material, wherein they replace the anions bound to the material previously, e.g. in regeneration. Alkali metal or alkaline-earth metal formate can be eluted from the material by feeding an alkali metal or alkaline-earth metal salt of the anion which replaces the formate anion to the material. The selectivity of the anions used in the process towards the anion exchange material decreases in the following order:

$$A > HCOO^- > D,$$

in which D is an anion which is replaced with formate at the first stage, and A is an anion whose alkali metal or alkaline-earth metal salt is supplied to elute alkali metal or alkaline-earth metal formate, respectively, from the anion exchanger. For example, the order of selectivity for a (strong-base) anion exchanger is the following (Helfferich, F., Ion Exchange, p. 168):

$$NO_3^- > I^- > Br^- > \underline{Cl^-} > \underline{HCOO^-} > CH_3COO^- > \underline{OH^-} > F^-$$

In the process, the anions passing through the anion exchange material are underlined. The anion exchanger cannot be directly converted from the Cl⁻ form back to the formate form because of unadvantageous selectivity, but it must first be converted to OH⁻ form in a separate regeneration step.

The following is a description of a method according to a preferred embodiment step by step, relating to the manufacture of potassium formate.

An anion exchange, which contains Cl ions as a result of elution of potassium formate out in a preceding step, is first converted to OH⁻ form with NaOH:

$$R\text{—}Cl + NaOH \rightleftharpoons R\text{—}OH + NaCl \quad (1)$$

With weak-base anion exchangers, it is also possible to use $NH_4OH$ as the hydroxide source.

After this, the formate ions are bound from a sodium formate solution to an ion exchange bed which contains anion exchange material. Instead of a sodium formate solution, it is possible to use a formic acid solution. It is also possible to use a mixture of formic acid and sodium formate. Similarly, it is possible to use any substance whose aqueous solution contains formate ions and whose aqueous solution is not too alkaline, if a weak-base anion exchanger is used.

$$R\text{—}OH + HCOONa \rightleftharpoons R\text{—}HCOO + NaOH, \text{ or}$$
$$R\text{—}OH + HCOOH \rightleftharpoons R\text{—}HCOO + H_2O \quad (2)$$

By changing the anion exchanger back to Cl⁻ form, a KCl solution can be used to elute potassium formate out of the anion exchange material:

$$R\text{—}HCOO + KCl \rightleftharpoons R\text{—}Cl + HCOOK \quad (3)$$

After this, the same anion exchange material can be used again by replacing chloride with hydroxide according to step (1). Sodium hydroxide eluted out in step (2) can thus be recirculated to step (1). After each step, washing with water is performed. The washing can be intensified by raising the temperature.

In different steps of the process, solutions are used whose concentration is in the range from 0.1 to 5 M. Also, in the elution of potassium formate from the anion exchanger, the concentration of potassium salt solutions used can be in the range from 0.1 to 5 M.

Ion exchange for producing potassium formate can take place in a temperature range from 0 to 110° C., typically from 20 to 60°C.

In a way analogical to that presented above, it is possible to prepare calcium formate. The reactions (1) and (2) take place as above, but in the reaction (3), the anion exchanger is converted to chloride form with a calcium chloride solution:

2R—HCOO+CaCl$_2$⇌2R—Cl+(HCOO)$_2$Ca

According to an advantageous alternative, the manufacturing process, in which the same anion exchanger is used several times, is as follows:

Use is made of an anion A, whose selectivity to the anion exchange material is higher than that of formate, and an anion D, whose selectivity to the anion exchange material is lower than that of formate.

Use is made of a starting agent containing formic acid and/or a formic acid salt whose cation (starting agent cation) is different from the cation of the alkali metal or alkaline-earth metal formate (product cation).

In the first step, the anion exchanger is regenerated by feeding into it a solution that contains the anion D, wherein the anion A left therein at the production stage can be eluted from the anion exchanger.

In the second step, a solution that contains the formate anion, such as formic acid and/or a formic acid salt whose cation is the starting agent cation, is fed into the anion exchanger.

In the third step, i.e. the production step, a solution which contains the anion A and in which the cation is the product cation, is fed into the anion exchanger.

All the steps are implemented in such a way that the solution is fed in a continuous flow through the anion exchange material, and the anion exchange between the solid anion exchanger and the solution takes place during this flow. The anion exchanger is preferably in a flow-through column, through which the solution is led. The solutions to be led in subsequent steps through the anion exchanger are preferably aqueous solutions.

These steps can be repeated several times in succession for the same anion exchanger. Furthermore, it is possible to circulate the anion D eluted in the second step to the first step, i.e. to the regeneration step. If in the second step the feeding solution contains a formate whose cation is the starting agent cation, a regeneration solution is obtained which contains the anion D and the starting agent cation.

Strong-base anion exchangers act in the pH range from 0 to 14, whereas the active range of weak-base anion exchangers is in the pH range from 0 to 9. Consequently, when selecting the formate ion source, one should take into account the strength of the ion exchange resin and the resulting active pH range. In a strong-base anion exchanger, the functional group is generally a quaternary ammonium ion, which is trimethylamine in type I and dimethyl-β-hydroxyethylamine in type II presented below.

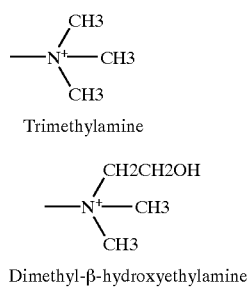

Type I

Trimethylamine

Type II

Dimethyl-β-hydroxyethylamine

Type I is slightly more basic than type II, i.e. the anions are slightly more firmly bonded to the anion exchanger of type I. Consequently, the regeneration of type II to the OH$^-$ form is slightly easier. In type II, the chemical stability and temperature resistance is slightly lower than in type I.

In a weak-base anion exchanger, the functional group is generally a tertiary amine—N(CH$_3$)$_2$.

Solid ion exchangers exist in various forms, having different porous structures and being based on different polymers. This invention is not dependent on the form, porous structure or polymer. The shape of the ion exchanger can be e.g. sphere, powder, fibre, or flake. Macroporous or gel-like ion exchanger resins work.

The invention will be described in the following examples which do not restrict the invention. The formate content is determined by ion chromatography according to the standard SFS-EN ISO 10304-01, and the chloride content by a chloride-selective electrode. The volume of the eluted solution is given in bed volumes BV, which in the tests was 100 ml or 200 ml. The water used, in which also the solutions were prepared, was ion-exchanged water whose conductivity was less than 3 μS/cm.

EXAMPLE 1

Strong-base Anion Exchanger at 22° C., 1 M KCl Solution

The test was made with a strong gel-like type I anion exchanger Amberlite IRA400 (an anion exchanger based on polystyrene cross-linked with divinylbenzene, manufactured by Rohm and Haas Company) in an ion exchange column, wherein bed height was 50 mm and diameter 50 mm. The bed had been converted to formate form with 1 M sodium formate. 1 M KCl solution was fed into an HCOO$^-$ form ion exchange resin bed, thermostated at the temperature of 22° C., at a rate of 11 ml/min, wherein a potassium formate pulse could be eluted from the bed. This is shown in FIG. 1. The yield was 0.174 mol, of which 95% had a purity of 57% and 100% had a purity of 45%.

Figure 9:
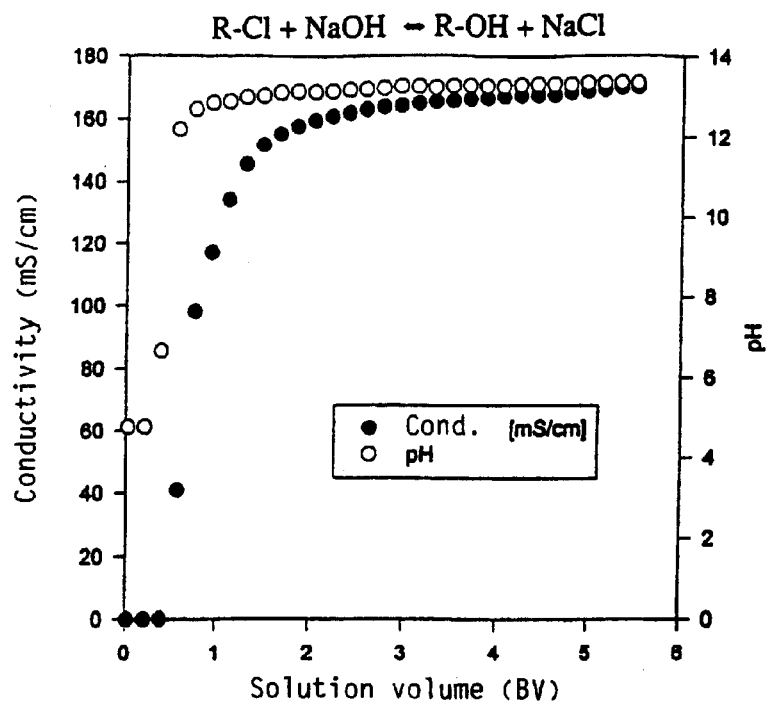
Figure 10:
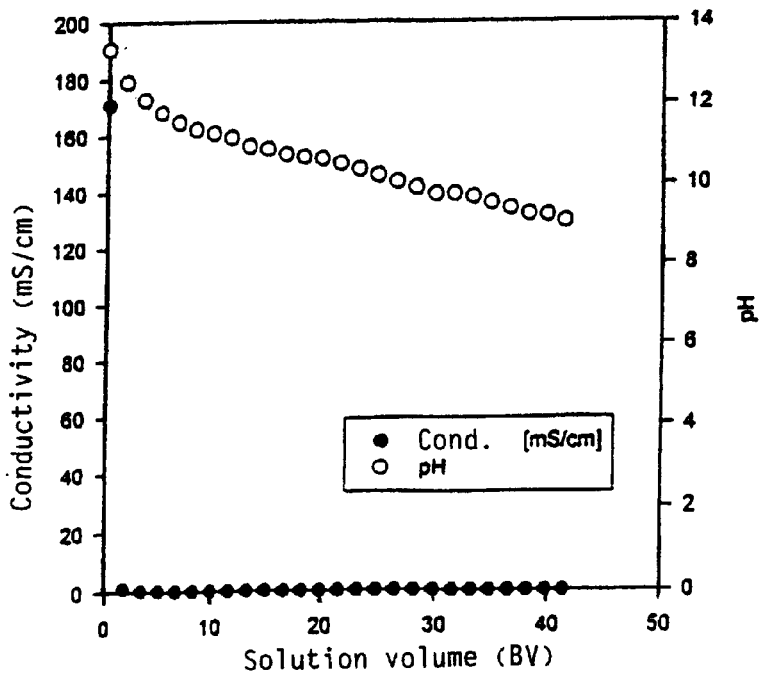
Figure 11:
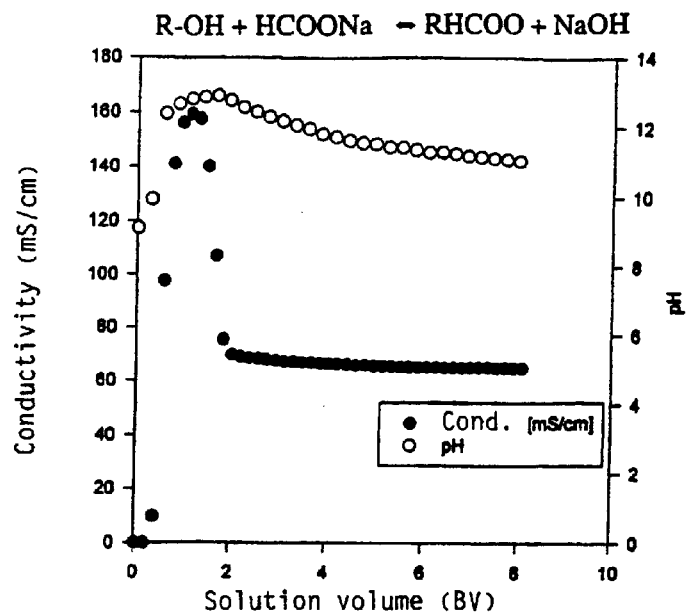
Figure 12:
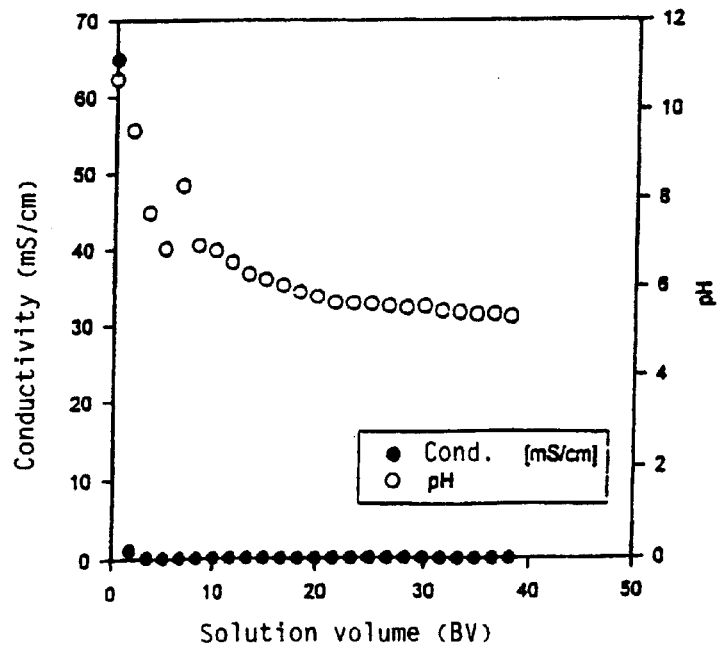

FIGS. 9 to 12 illustrate other steps of the process. FIG. 9 shows the pH and the conductivity of the flow coming from the ion exchange bed, when the resin in the Cl$^-$ form was converted to OH$^-$ form with 1 M NaOH, the flow rate being 11 ml/min. FIG. 10 shows washing of the resin in the OH$^-$ form with ion exchanged water in concurrent direction at a flow rate of 33 ml/min. The conductivity of 4 mS/cm was obtained with a water quantity of about 42 BV. FIG. 11 shows the exchange of resin in the OH$^-$ form into formate form with 1 M HCOONa at the flow rate of 11 ml/min. FIG. 12 shows the washing of resin in formate form with ion exchanged water in concurrent direction at the rate of 33 ml/l.

The conductivity of 8 μS/cm was obtained with a water quantity of about 38 BV.

EXAMPLE 2

Strong-base Anion Exchanger at 25° C., 4 M KCl Solution

Figure 2:
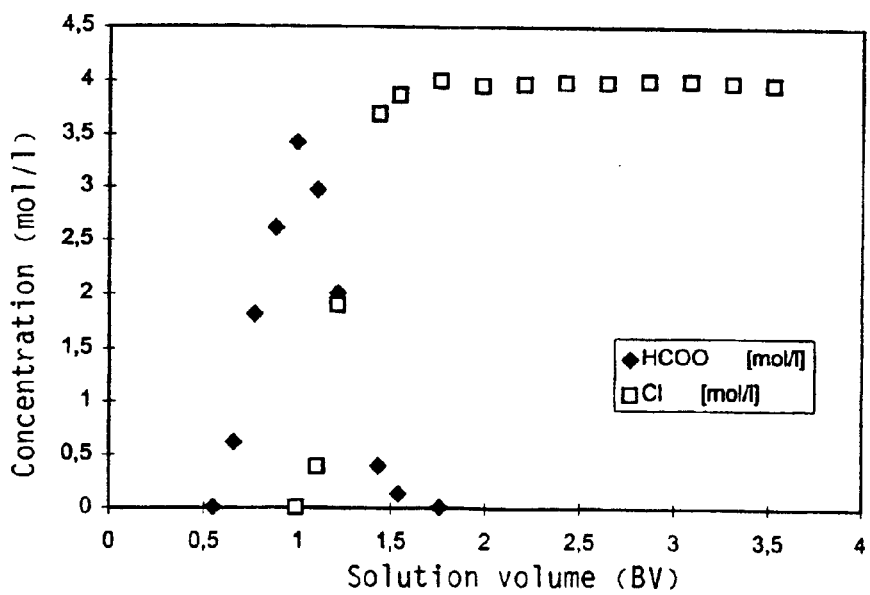

The test was made with a strong-base gel-like type I anion exchanger Amberlite IRA-400 in an ion exchange column, wherein bed height was 50 mm and diameter 50 mm. The bed had been converted to formate form with 1 M sodium formate. 4 M KCl solution was fed into an $HCOO^-$ form ion exchange resin bed, thermostated at the temperature of 25° C., at a rate of 11 ml/min, wherein a potassium formate pulse was eluted from the bed. This is shown in FIG. 2. The yield was 0.167 mol, of which 95% had a purity of 44% and 100% had a purity of 24%.

EXAMPLE 3
Strong-base Anion Exchanger at 50° C., 4 M KCl Solution

Figure 3:
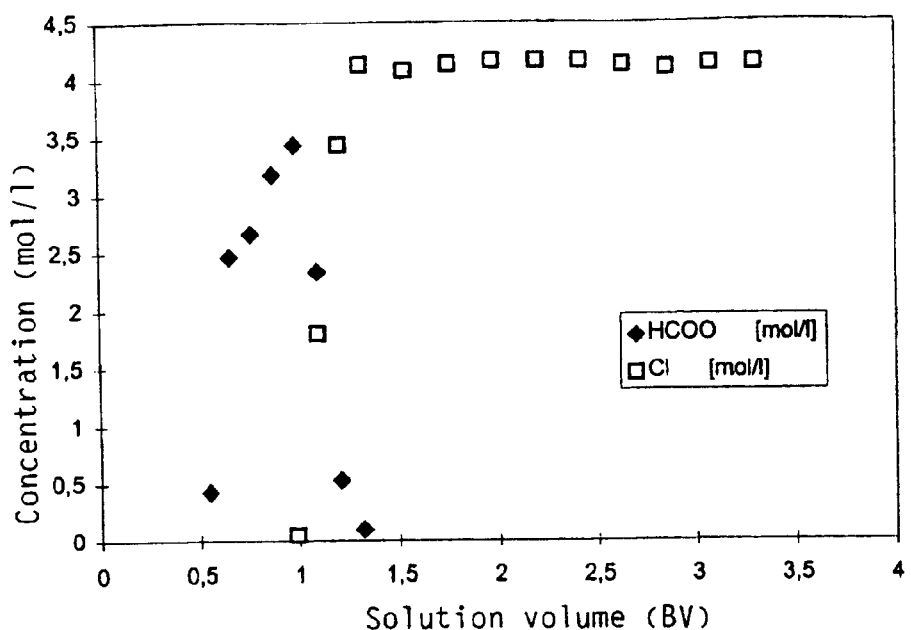

The test was made with a strong-base gel-like type I anion exchanger Amberlite IRA400 in an ion exchange column, wherein bed height was 50 mm and diameter 50 mm. The bed had been converted to formate form with 1 M sodium formate, 4 M KCl solution was fed into an $HCOO^-$ form ion exchange resin bed, thermostated at the temperature of 50° C., at a rate of 11 ml/min, wherein a potassium formate pulse was eluted from the bed. This is shown in FIG. 3. The yield was 0.166 mol, of which 95% had a purity of 69% and 100% had a purity of 47%.

EXAMPLE 4
Weak-base Anion Exchanger at 25° C., 1 M KCl Solution

Figure 4:
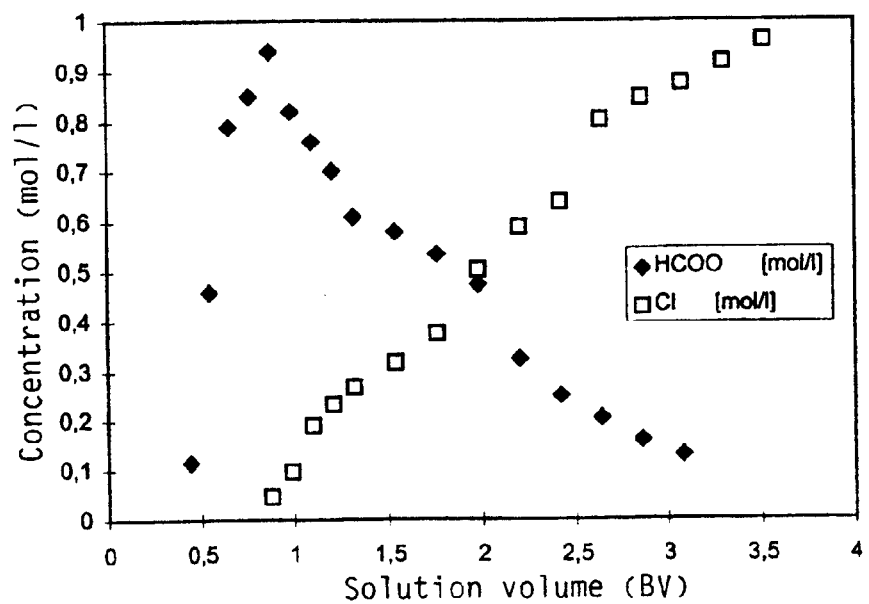

The test was made with a weak-base, macroporous anion exchanger DIAION WA30 based on a polystyrene copolymer cross-linked with divinylbenzene, manufactured by Mitsubishi Chemicals Corp., in an ion exchange column, wherein bed height was 50 mm and diameter 50 mm. Differently from the previous examples, the bed had been converted to formate form with a mixture of 0.5 M sodium formate and 0.5 M formic acid. 1 M KCl solution was fed into an $HCOO^-$ form ion exchange resin bed, thermostated at the temperature of 25°C., at a rate of 11 ml/min, wherein a potassium formate pulse was eluted from the bed. This is shown in FIG. 4. The yield was 0.127 mol, of which 95% had a purity of 23% and 100% had a purity of 16%.

EXAMPLE 5
Strong-base Anion Exchanger at 22° C., 1 M KCl Solution

Figure 5:
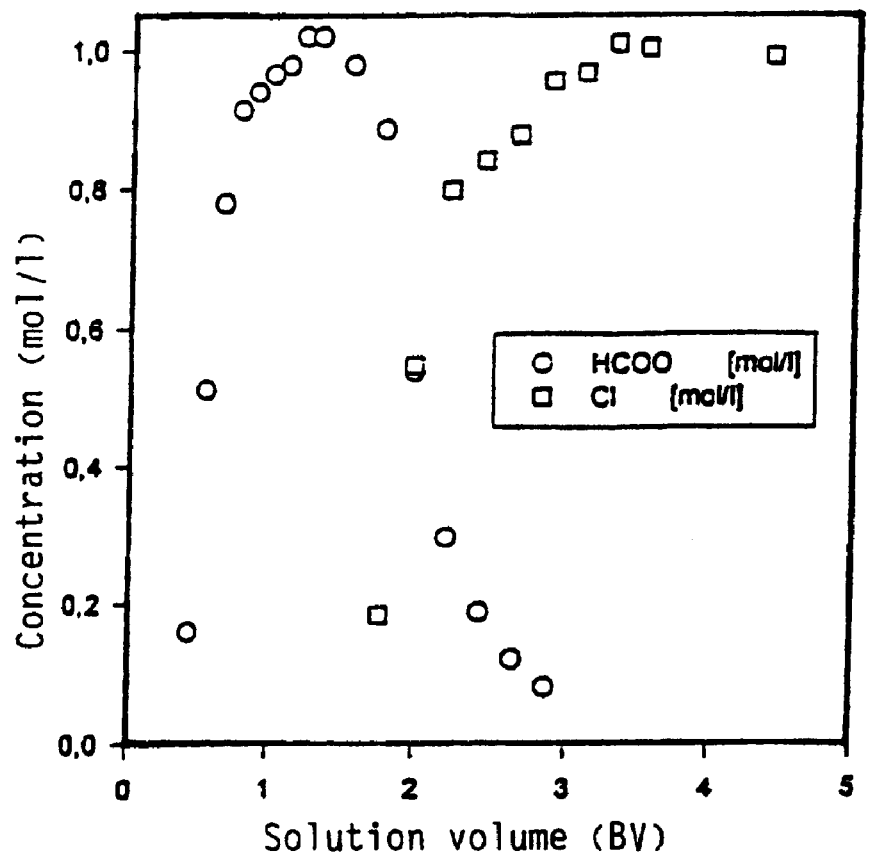

The test was made with a strong-base gel-like type II anion exchanger Amberlite IRA-410 (an anion exchanger based on polystyrene cross-linked with divinylbenzene, manufactured by Rohm and Haas Company) in an ion exchange column, wherein bed height was 50 mm and diameter 50 mm. The bed had been converted to formate form with 1 M sodium formate. 1 M KCl solution was fed into an $HCOO^-$ form ion exchange resin bed, thermostated at the temperature of 22° C., at a rate of 11 ml/min, wherein a potassium formate pulse could be eluted from the bed. This is shown in FIG. 5.

EXAMPLE 6
Weak-base Anion Exchanger at 22° C., 1 M KCl Solution

Figure 6:
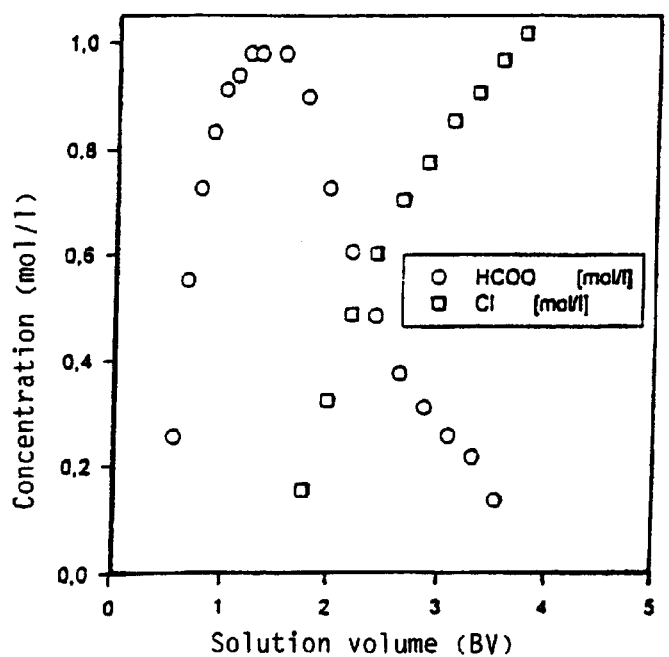

The test was made with a weak-base macroporous anion exchanger Amberlite IRA-67 (an anion exchanger based on polyacrylate cross-linked with divinyl benzene, manufactured by Rohm and Haas Company) in an ion exchange column, wherein bed height was 50 mm and diameter 50 mm. The bed had been converted to formate form with 1 M sodium formate. 1 M KCl solution was fed into an $HCOO^-$ form ion exchange resin bed, thermostated at the temperature of 22° C., at a rate of 11 ml/min, wherein a potassium formate pulse could be eluted from the bed. This is shown in FIG. 6.

EXAMPLE 7
Strong-base Anion Exchanger at 50° C., 4 M KCl Solution

Figure 7:
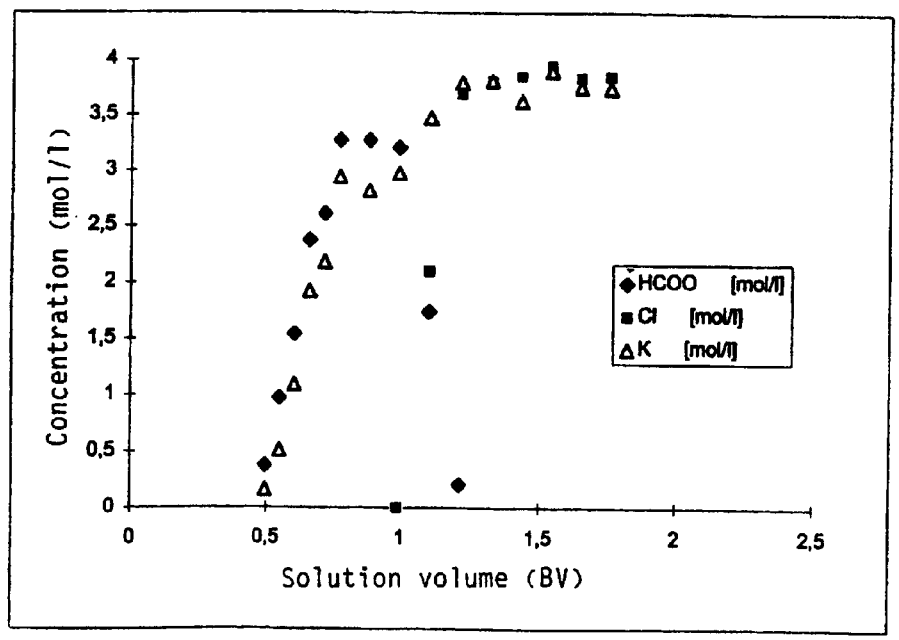

The test was made with a strong-base gel-like type I anion exchanger Amberlite IRA400 in an ion exchange column, wherein bed height was 100 mm and diameter 50 mm. The bed had been converted to formate form with 1 M sodium formate. 4 M KCl solution was fed into an $HCOO^-$ form ion exchange resin bed, thermostated at the temperature of 50° C., at a rate of 11 ml/min, wherein a potassium formate pulse was eluted from the bed. This is shown in FIG. 7.

Figure 8:
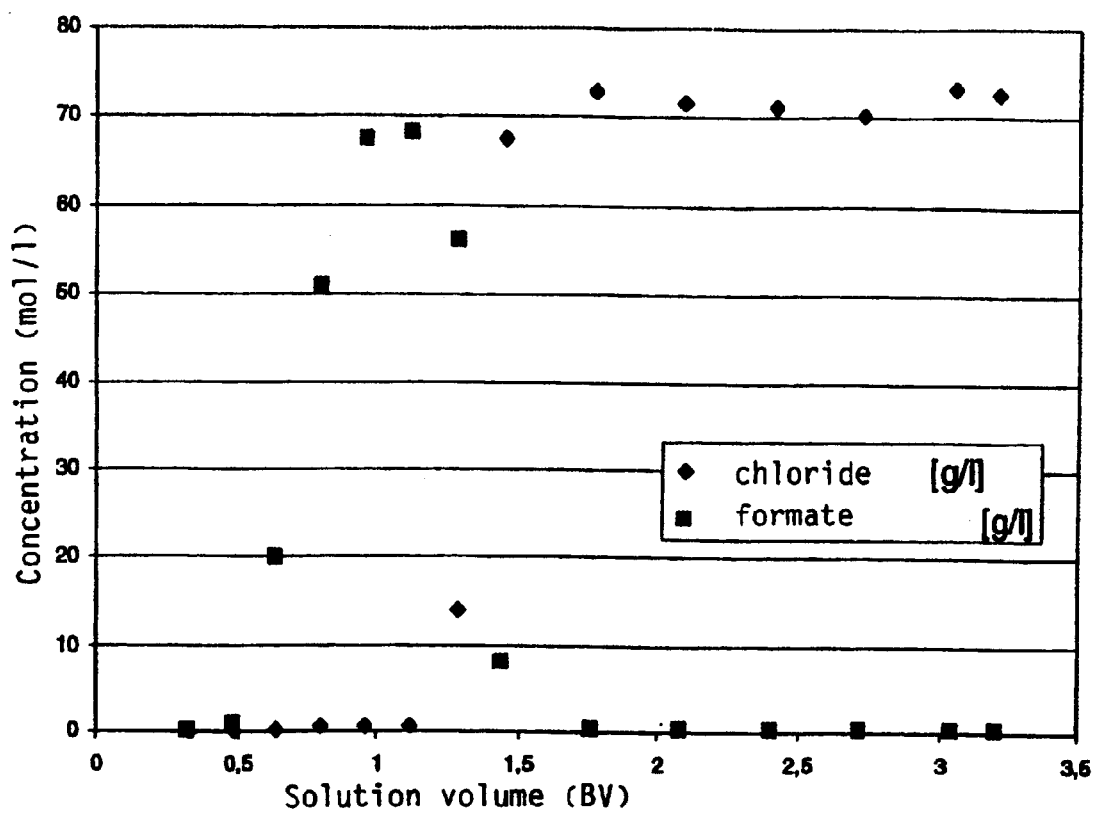

EXAMPLE 8
Strong-base Anion Exchanger at 22° C., 1 M $CaCl_2$ Solution in the Manufacture of Calcium Formate $(HCOO)_2Ca$ The test was made with a strong-base macroporous type I anion exchanger in an ion exchange column, wherein bed height was 320 mm and diameter 26 mm. The bed had been converted to formate form with 1 M sodium formate. In the test carried out at the temperature of 22° C., 1 M $CaCl_2$ solution was fed into an $HCOO^-$ form ion exchange resin bed at a rate of 9 ml/min, wherein a calcium formate pulse was eluted from the bed. This is shown in FIG. 8. The yield was 0.162 mol, which corresponds to 98% of the total capacity of the bed with the resin in question.

As can be seen from FIGS. 1 to 8, formate comes clearly before chloride in the flow eluted from the anion exchange material. Both a strong-base and a weak-base anion exchange resin are thus suitable for the manufacture of potassium formate or calcium formate. A strong resin is more advantageous in that it releases the alkali metal or alkaline-earth metal formate faster than a weak-base resin, and a pure product is recovered in a more advantageous way. Furthermore, it can be washed faster between the steps of ion exchange.

In practice, it is possible to produce a pure alkali metal or alkaline-earth metal formate by stopping the recovery of the outcoming flow for production purposes at the stage when chloride is detected in the flow eluted from the anion exchange material. Similarly, it is also possible to optimize the process in other ways. For example, after regeneration with an OH ion, it is advantageous to wash the ion exchanger material with water in countercurrent direction, because it requires less water than concurrent washing. In continuous production, it is advantageous to arrange several anion exchangers existing in different steps in parallel, of which at least one anion exchanger can be used for potassium formate production and for which the above-described steps can be repeated several times in succession.

The invention is not limited to a specific solid ion exchanger structure, but it can be modified within the scope of the inventive idea disclosed in the appended claims. Solid ion exchangers exist in various forms, having different porous structures and being based on different polymers. The solid ion exchanger material can consists of spheres, powder, fibres, flakes, or other suitable bodies. Furthermore, the invention is not limited to a specific porous structure, but e.g. both macro-porous and gel-type ion exchangers can be used without deviating from the basic idea of the invention.

What is claimed is:

1. Method for industrial manufacturing alkali metal or alkaline-earth metal formate, starting from a formate anion, characterized in that the method comprises at least the following sequentially performed steps:

A) conversion of a solid strong-base anion exchanger to formate form by feeding into it a solution containing a formate anion, which replaces an anion less selective to the anion exchanger than the formate anion, B) exchanging the formate anion in the anion exchanger for a replacing anion by feeding into it an alkali metal or alkaline-earth metal salt solution of this replacing anion, which is more selective to the anion exchanger than the formate anion;

C) recovering the alkali metal or alkaline-earth metal formate solution eluted from the anion exchanger during the exchange of the formate anion; and D) exchanging the replacing anion left in the anion exchanger in step B for an anion less selective to the anion exchanger than said replacing anion by feeding into the anion exchanger a solution of said less selective anion, which will be replaced in step A with the formate anion that is more selective to the anion exchanger;

wherein all of the steps being conducted by feeding the solutions in a continuous flow through the anion-exchange material and repeating steps A through D several times in succession for the same anion exchanger.

2. The method according to claim 1, characterized in that the anion exchanger is converted to formate form by feeding into it a sodium formate solution, a formic acid solution or a solution which contains both sodium formate and formic acid.

3. The method according to claim 1 characterized in that the anion less selective to the anion exchanger is a hydroxide anion.

4. The method according to claim 1, characterized in that the replacing anion which is more selective to the anion exchanger is a chloride anion.

5. The method according to claim 1, characterized in that the functional group of the anion exchanger is a quaternary ammonium ion.

6. The method according to claim 1, characterized in that the anion exchanger used is a gel-like or macro-porous anion exchanger.

7. The method according to claim 1, characterized in that the concentration of the alkali metal or alkaline-earth metal salt solution supplied to the anion exchanger is 0.1 to 5M.

8. The method according to claim 1, characterized in that the ion exchange for producing an alkali metal or alkaline-earth metal formate takes place at a temperature of 0–110° C., preferably 20–60° C.

9. The method according to claim 1, characterized in that in the different steps, aqueous solutions are used.

10. The method according to claim 1, characterized in that the alkali metal is potassium.

11. The method according to claim 1, characterized in that the alkaline-earth metal is calcium.

12. The method according to claim 1, wherein a solution obtained from the anion exchanger during the conversion to formate form contains the less selective anion and is recirculated to step D.

* * * * *